(12) United States Patent
Bedoya-Zurita et al.

(10) Patent No.: US 6,262,060 B1
(45) Date of Patent: Jul. 17, 2001

(54) AZACYCLOALKANE DERIVATIVES, PREPARATION AND THERAPEUTIC APPLICATION

(75) Inventors: Manuel Bedoya-Zurita, Châteaudouble (FR); Juan Antonio Diaz Martin, Madrid (ES); Marc Daumas, Neauphle le Château (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/673,027

(22) PCT Filed: Apr. 13, 1999

(86) PCT No.: PCT/FR99/00851

§ 371 Date: Nov. 27, 2000

§ 102(e) Date: Nov. 27, 2000

(87) PCT Pub. No.: WO99/52876

PCT Pub. Date: Oct. 21, 1999

(30) Foreign Application Priority Data

Apr. 15, 1998 (FR) .................................................. 98 04653

(51) Int. Cl.$^7$ ...................... C07D 221/20; C07D 495/10; C07D 209/44; A61K 31/44; A61K 31/40
(52) U.S. Cl. .......................... 514/278; 514/319; 514/409; 514/416; 544/58.4; 544/171; 544/386; 546/16; 546/19; 546/203; 546/205; 546/208; 546/214; 548/408; 548/434; 548/453; 548/470
(58) Field of Search ................................. 546/16, 19, 203, 546/205, 208, 214; 544/58.4, 171, 386; 548/408, 434, 453, 470; 514/278, 319, 409, 416

(56) References Cited

U.S. PATENT DOCUMENTS

| 5,280,122 | 1/1994 | Chiu et al. . |
| 5,869,518 | 2/1999 | Zurita et al. ........................ 546/221 |

FOREIGN PATENT DOCUMENTS

| 507 534 | 10/1992 | (EP) . |
| 661 292 | 7/1995 | (EP) . |
| 92/20685 | 11/1992 | (WO) . |
| 96/34870 | 11/1996 | (WO) . |

OTHER PUBLICATIONS

Derwent Patent Abstract No. 063821 (1995).
Derwent Patent Abstract No. 063820 (1995).
Patent Abstract of Japan, vol. 18, No. 385 (C–1227) (1994).
Derwent Patent Abstract No. 185860 (1994).
Derwent Patent Abstract No. 410827 (1993).
Derwent Patent Abstract No. 199247 (1992).

*Primary Examiner*—Bernard Dentz
(74) *Attorney, Agent, or Firm*—Michael D. Alexander

(57) ABSTRACT

The invention relates to azacycloalkane derivatives, to pharmaceutical compositions containing them, to processes for preparing them, and to methods for the treatment of hyperglycaemia, diabetes, obesity or inflammation utilizing them.

37 Claims, No Drawings

AZACYCLOALKANE DERIVATIVES, PREPARATION AND THERAPEUTIC APPLICATION

This application is a 371 of PCT/FR99/00851 filed Apr. 13, 1999.

The subject of the present invention is azacycloalkane derivatives, their preparation and their therapeutic application, especially in the treatment of diabetes, obesity, hyperglycaemia and inflammation.

The azacycloalkane derivatives of the invention correspond to the general formula (I)

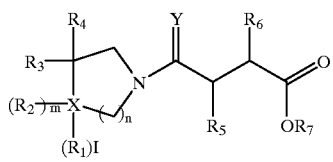

in which:

$R_1$ represents a hydrogen atom, hydroxyl, a $C_{1-4}$ alkyl, $C_{1-4}$ hydroxyalkyl, $C_{4-7}$ cycloalkyl or $C_{1-4}$ alkyloxy($C_{1-4}$ alkyl) group, an aminocarbonyl group, a benzyl, a heterocycloalkyl or heteroaryl group comprising from 4 to 5 carbon atoms and a heteroatom, such as nitrogen, sulphur or oxygen, the heterocycloalkyl or heteroaryl group being optionally substituted with one or two substituents such as a hydroxyl, a $C_{1-4}$ alkyl group or a halogen;

$R_2$, $R_3$ and $R_4$, which may be identical or different, represent independently of each other a hydrogen atom, a $C_{1-4}$ alkyl group, a $C_{4-7}$ cycloalkyl group, a hydroxyl group, an aminocarbonyl group or a heteroaryl group comprising from 4 to 5 carbon atoms and a heteroatom such as nitrogen, sulphur or oxygen, the heteroaryl group being optionally substituted with one or two substituents such as a hydroxyl group, a $C_{1-4}$ alkyl group or a halogen;

or $R_1$ and $R_2$ together form a $C_{3-6}$ alkylene group, a $C_{2-3}$ alkylenedioxy group, a $C_{2-3}$ alkylenedithio group, —(O$_2$)S—$C_{2-3}$ alkylene-S(O$_2$)— or a group —CH$_2$NHC(O)CH$_2$—;

or $R_2$ and $R_3$ together form a propylene or butylene group, a $C_{1-3}$ alkylenedioxy group, a carbonyldioxy group or a 2-butenylene;

or $R_2$ and $R_3$ together form with the atoms carrying them a norbornane or a 5-norbornene or a bond in order to give a double bond between the atoms carrying them, X being a carbon atom;

$R_5$ represents a hydrogen atom, a hydroxyl group or, when $R_6$ represents a hydrogen, a 1-indanyl group;

$R_6$ represents an aromatic group chosen from the following groups:

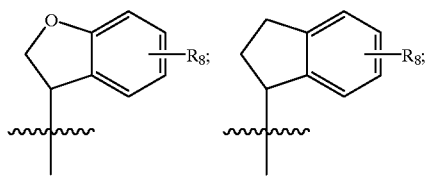

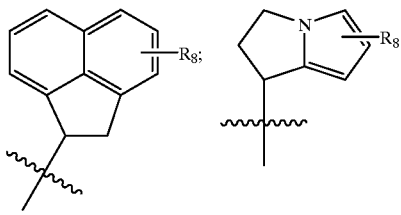

or, when $R_2$ and $R_3$ together form a $C_{1-3}$ alkylenedioxy or carbonyldioxy group, a benzyl optionally substituted with one or two substituents such as a halogen or a $C_{1-4}$ alkyl group, or $R_6$ represents a hydrogen, when $R_5$ represents a 1-indanyl group;

$R_7$ represents a hydrogen atom or a $C_{1-4}$ alkyl group;

$R_8$ represents a hydrogen, an acetyl, a benzoyl, a $C_{1-4}$ alkyl group, optionally substituted with a hydroxyl; or a $C_{1-2}$ alkylphenyl group, optionally substituted on the alkyl group with a hydroxyl, X represents a carbon, nitrogen, oxygen or sulphur atom or a sulphonyl group, Y represents an oxygen or sulphur atom, n is equal to 1 or 2; l is equal to 1 and m is equal to 0 when X represents a nitrogen atom; l and m are equal to 0 when X represents a sulphur or oxygen atom or a sulphonyl; they are equal to 1 when X represents a carbon atom.

Within the framework of the present invention:

$C_{x-y}$ is understood to mean a carbon chain which may have from x to y carbon atoms;

alkyl is understood to mean a linear or branched saturated aliphatic group; for example, a $C_{1-4}$ alkyl group represents a linear or branched carbon chain of 1 to 4 carbon atoms, more particularly a methyl, ethyl, propyl, isopropyl, butyl, isobutyl and tert-butyl radical, the term $C_{x-y}$ alkylene denoting a divalent $C_{x-y}$ alkyl group;

$C_{x-y}$ alkenyl is understood to mean a linear or branched aliphatic group comprising from x to y carbon atoms and 1 or 2 ethylenic unsaturations, the term $C_{x-y}$ alkenylene denoting a divalent $C_{x-y}$ alkenyl group;

cyclo($C_{x-y}$ alkyl) is understood to mean a cyclic radical comprising x to y carbon atoms;

alkoxy is understood to mean an alkyloxy group containing a linear or branched saturated aliphatic chain;

halogen atom is understood to mean a fluorine, a chlorine, a bromine or an iodine;

heteroaryl is understood to mean a pyrrolyl, pyridyl, thyenyl, furyl or pyranyl group, preferably a pyrrolyl group; and heterocycloalkyl is understood to mean a pyrrolidinyl, piperidyl, tetrahydrofuranyl and tetrahydropyranyl group, preferably a tetrahydrofuranyl group.

The compounds of formula (I) can form with pharmaceutically acceptable acids and bases salts which form part of the invention. In particular, the compounds for which $R_7$ is a hydrogen can form salts with bases. The preferred salts of bases are, in this case, the salts of sodium and of calcium, which are such that $R_7$ represents a sodium or calcium atom.

The compounds of formula (I) possess one or more asymmetric carbon atoms; they may exist in the form of enantiomers, diastereoisomers or of mixtures of these various forms, including racemic mixtures which form part of the invention.

The preferred compounds according to the invention are those for which:

$R_2$, $R_3$ and $R_4$, when they are not linked together, represent, independently of each other, a hydrogen atom, a $C_{1-4}$ alkyl group or a hydroxyl group, and/or the compounds for which $R_8$ represents a hydrogen.

Among these, the compounds for which $R_4$ represent a hydrogen are particularly preferred and in particular those for which $R_5$ represents a hydrogen.

Moreover, the compounds for which $R_6$ represents an aromatic group other than a benzyl, more especially an indanyl, are also preferred and in particular those containing the abovementioned preferred groups. Among the latter, $R_1$ and $R_2$ preferably form a $C_{3-6}$ alkylene group, more especially a $C_4$ alkylene group.

The compounds of formula (I) may be prepared according to the process represented in scheme 1.

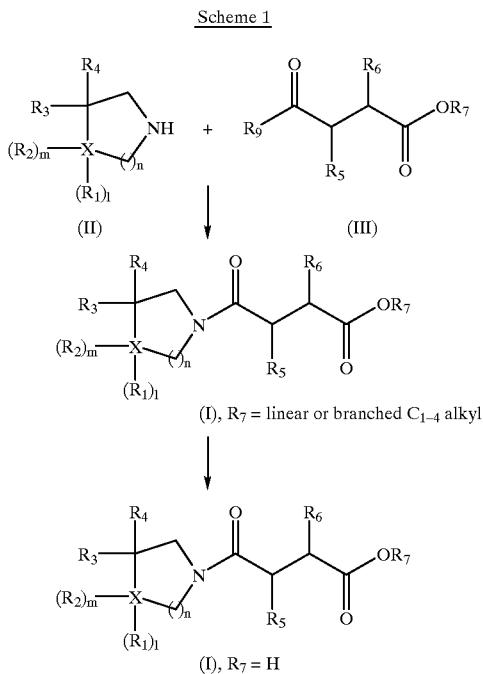

According to this process, the compounds of formula (I), in which Y represents an oxygen and $R_7$ represents a $C_{1-4}$ alkyl group, are prepared by reacting a compound of general formula (II)

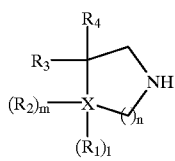

in which $R_1$, $R_2$, $R_3$, $R_4$, X, l, m and n are defined as in formula (I), with a compound of general formula (III)

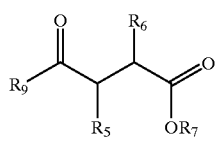

in which $R_7$ represents a $C_{1-4}$ alkyl group, $R_5$ and $R_6$ are defined as in formula (I) and $R_9$ represents a halogen atom, such as for example a chlorine or a bromine, or a hydroxyl group, in an aprotic solvent such as dichloromethane, in the presence of triethylamine and/or an acid function activating agent such as isobutyl chloroformate or carbonyldiimidazole.

The compounds of the invention of formula (I), for which Y is a sulphur atom and $R_7$ represents a $C_{1-4}$ alkyl group, may be obtained by reacting the compounds (I), previously obtained, with a thiation agent such as Lawesson's reagent.

The compounds of the invention of formula (I), for which $R_7$ is a hydrogen atom, may be obtained by hydrolysing the compounds (I), in which $R_7$ represents a $C_{1-4}$ alkyl group, according to methods known to persons skilled in the art, for example sodium hydroxide or hydrochloric acid method.

The compounds of formula (II) may be prepared according to processes well known to persons skilled in the art, or by methods described in the literature, such as, for example in Boll. Chim. Farm., 121 (1), 16–26 (1982), in J. Med. Chem., 33, 62–69 (1990) or in J. Heterocyl. Chem., 30, 1357–59 (1993).

The compounds of formula (III) may be prepared according to processes described in the literature, such as for example in J. Am. Chem. Soc., 90, 3495–3502 (1968) or in J. Med. Chem., 36, 2788–2797 (1993).

The following examples illustrate the invention without however limiting the scope of the claims. Analyses confirm the structure of the compounds.

EXAMPLE 1

[R-(R*,S*)]-α-(2,3-Dihydro-1H-inden-1-yl)-γ-oxo-8-azaspiro[4.5]decane-8-butanoic acid.

1.1.-1-Ethyl and 4-(1,1-dimethylethyl) [R-(R*,S*)]-2-(2,3-dihydro-1H-inden-1-yl)butanedioate.

141.5 ml (0.353 mol) of a 2.5 M solution of n-butyllithium in hexane are added at −70° C. to a solution of 49.5 ml (0.353 mol) of diisopropylamine in 400 ml of dry tetrahydrofuran; after 30 min, a solution of 60 g (0.294 mol) of ethyl (S)-2,3-dihydro-1H-indene-1-acetate (obtained according to the method described in application WO97/06155) in 200 ml of dry tetrahydrofuran is added; the mixture is stirred at −5° for 2.5 h, it is cooled to −70° C. and then 60.8 ml (0.411 mol) of tert-butyl bromoacetate are added and the mixture is stirred at room temperature for 16 h; 400 ml of a saturated ammonium chloride solution are added at 0° C., the mixture is stirred for 15 min and then extracted with twice 200 ml of ethyl acetate; the combined organic phases are washed with brine, dried over sodium sulphate and evaporated to dryness. After purification by distillation under vacuum (155–160° C. at 0.2 mmHg), 76.4 g of 1-ethyl and 4-(1,1-dimethylethyl) [R-(R*,S*)]-2-(2,3-dihydro-1H-inden-1-yl)butanedioate are obtained in the form of a yellowish oil; (R*,S*) diastereoisomeric ratio=⅕. Yield 82%. A solution of 54.3 g (0.17 mol) of the preceding product in 450 ml of tetrahydrofuran is cooled to −70° C.; 420 ml (0.42 mol) of a 1 M solution of sodium salt of 1,1,1,3,3,3-hexamethyldisilazane in tetrahydrofuran are added. The mixture is stirred at room temperature for 16 h, cooled to −70° C., 500 ml of saturated ammonium chloride solution are added, the mixture stirred for 15 min and then extracted with twice 150 ml of ethyl acetate; the combined organic phases are washed with brine, dried with sodium sulphate and evaporated to dryness. After purification by distillation under vacuum (145–155° C. at 0.2 mmHg), 39 g of 1-ethyl and 4-(1,1-dimethylethyl) [R-(R*,S*)]-2-(2,3-dihydro-1H-inden-1-yl)butanedioate are obtained in the form of a yellowish oil; (R*,S*) diastereoisomeric ratio=6/4. Yield 72%.

1.2.-1-Ethyl [R-(R*,S*)]-2-(2,3-dihydro-1H-inden-1-yl) butanedioate.

111 ml (1.44 mol) of trifluoroacetic acid are added at 0° C. to a solution of 39 g (0.122 mol) of 1-ethyl and 4-(1,1-dimethylethyl) [R-(R*,S*)]-2-(2,3-dihydro-1H-inden-1-yl) butanedioate in 600 ml of dichloromethane; the mixture is stirred at room temperature for 16 h and then evaporated to dryness; 32.47 g of 1-ethyl [R-(R*,S*)]-2-(2,3-dihydro-1H-inden-1-yl)butanedioate are obtained in the form of a reddish oil. The (R*,S*) diastereoisomeric ratio=6/4. Quantitative yield.

1.3.-Ethyl [R-(R*,S*)]-α-(2,3-dihydro-1H-inden-1-yl)-γ-oxo-8-azaspiro[4.5]decane-8-butanoate.

13 g (0.08 mol) of carbonyldiimidazole are added at 0° C. to a solution of 23.4 g (0.0735 mol) of 1-ethyl [R-(R*,S*)]-2-(2,3-dihydro-1H-inden-1-yl)butanedioate in 280 ml of dichloromethane; the mixture is stirred at room temperature for 1 h and then a solution of 14.2 g (0.08 mol) of 8-azaspiro[4.5]decane and 10.2 g (0.1 mol) of triethylamine in 340 ml of dichloromethane is added. The mixture is stirred for 16 h at room temperature, poured over 400 ml of cold water, the mixture is stirred for 15 min and then extracted with three times 150 ml of ethyl acetate; the combined organic phases are washed successively with 150 ml of saturated sodium hydrogen carbonate solution, with 150 ml of a 5% aqueous citric acid solution and then with brine, dried with sodium sulphate and evaporated to dryness. After purifying on a silica column with the aid of the ⅙ ethyl acetate/hexane eluent mixture, 24.57 g of ethyl [R-(R*,S*)]-α-(2,3-dihydro-1H-inden-1-yl)-γ-oxo-8-azaspiro[4.5] decane-8-butanoate are obtained in the form of a slightly yellow oil; (R*,S*) diastereoisomeric ratio=6/4. Yield 87%.

1.4.-[R-(R*,S*)]-α-(2,3-Dihydro-1H-inden-1-yl)-γ-oxo-8-azaspiro[4.5]decane-8-butanoic acid.

A solution of 6.8 g (0.17 mol) of sodium hydroxide in 60 ml of water is added to a solution of 20 g (0.0522 mol) of ethyl [R-(R*,S*)]-α-(2,3-dihydro-1H-inden-1-yl)-γ-oxo-8-azaspiro[4.5]decane-8-butanoate in a mixture of 150 ml of tetrahydrofuran and 150 ml of methanol, and the mixture is stirred for 3 h at 60° C. The mixture is concentrated, 200 ml of water are added, the solution obtained is washed with twice 150 ml of diethyl ether and then acidified at 0° C. with 6 M hydrochloric acid to pH 2 and it is extracted with twice 250 ml of dichloromethane; the organic phases are washed with brine, dried with sodium sulphate and evaporated to dryness. 16 g of [R-(R*,S*)]-α-(2,3-dihydro-1H-inden-1-yl)-γ-oxo-8-azaspiro[4.5]decane-8-butanoic acid are obtained in the form of a colourless oil; the (R*,S*) diastereoisomeric ratio=6/4. Yield 86%; 14 g (0.0295 mol) of this acid are dissolved in 320 ml of ethyl acetate, the solution is cooled to 0° C. and then a solution of 3.57 g (0.0295 mol) of (R) (+)-α-methylbenzylamine in 25 ml of ethyl acetate is added; the mixture is stirred at room temperature for 16 h, the precipitate formed is filtered, it is stirred in 30 ml of ethyl acetate, it is filtered and then it is dried; 7 g of a white solid of melting point 155–156° C. are obtained; 75 ml of water are added to a suspension of 7 g of the preceding solid, the solution is cooled to 0° C. and acidified with 6 M hydrochloric acid to pH 2; the mixture is stirred for 15 min with 170 ml of diisopropyl ether, the organic phase is decanted off and the aqueous phase is extracted with 170 ml of diisopropyl ether; the organic phases are washed with brine, dried over sodium sulphate and then evaporated to dryness. 4.9 g of [R-(R*,S*)]-α-(2,3-dihydro-1H-inden-1-yl)-γ-oxo-8-azaspiro[4.5]decane-8-butanoic acid are obtained in the form of a white solid; (R*,S*) diastereomeric ratio >99%. The product melts at 137° C. with decomposition. $[\alpha]_D$=−26° (c=5%, ethanol)

EXAMPLE 2
Calcium [R-(R*,S*)]-α-(2,3-dihydro-1H-inden-1-yl)-γ-oxo-8-azaspiro[4.5]decane-8-butanoate 3 ml (0.04 mol) of a 25% ammonium hydroxide solution are added to a suspension of 4.5 g (0.0126 mol) of [R-(R*,S*)]-α-(2,3-dihydro-1H-inden-1-yl)-γ-oxo-8-azaspiro[4.5] decane-8-butanoic acid in 225 ml of water, the mixture is stirred for 20 min and then a solution of 1 g (0.009 mol) of calcium chloride in 25 ml of water is added dropwise; the mixture is stirred for 1.5 h, the precipitate formed is filtered, it is washed with cold water and then it is dried under vacuum. 4.2 g of calcium [R-(R*,S*)]-α-(2,3-dihydro-1H-inden-1-yl)-γ-oxo-8-azaspiro[4.5]decane-8-butanoate are obtained in the form of a white solid; (R*,S*) diastereomeric ratio >99%. Yield 89%. Melting point 231–233° C. $[\alpha]_D$=−8° (c=2.5%, dimethyl sulphoxide)

EXAMPLE 3
[S-(S*,S*)]-α-(2,3-Dihydro-1H-inden-1-yl)-γ-oxo-8-azaspiro[4.5]decane-8-butanoic Acid This compound was prepared according to the process described in Example 1, using (S)(−)-α-methylbenzylamine as resolving reagent. The [S-(S*,S*)]-α-(2,3-dihydro-1H-inden-1-yl)-γ-oxo-8-azaspiro[4.5]-decane-8-butanoic acid exists as a white solid which melts at 144–146° C. with decomposition. $[\alpha]_D$=+22° (c=5%, ethanol).

EXAMPLE 4
[R-(R*,R*)]-α-(2,3-Dihydro-1H-inden-1-yl)-γ-oxo-8-azaspiro[4.5]decane-8-butanoic Acid This compound was prepared according to the process described in Example 1, using ethyl (R)-2,3-dihydro-1H-indene-1-acetate as starting material. The [R-(R*,R*)]-α-(2,3-Dihydro-1H-inden-1-yl)-γ-oxo-8-azaspiro[4.5]decane-8-butanoic acid exists as a white solid which melts at 139–141° C. $[\alpha]_D$=−19.2° (c=5%, ethanol).

EXAMPLE 5
[S-(S*,R*)]-α-(2,3-Dihydro-1H-inden-1-yl)-γ-oxo-8-azaspiro[4.5]decane-8-butanoic Acid.

This compound was prepared according to the process of Example 4, using (S)(−)-α-methylbenzylamine as resolving reagent. The [S-(S*,R*)]-α-(2,3-dihydro-1H-inden-1-yl)-γ-oxo-8-azaspiro[4.5]decane-8-butanoic acid exists as a white solid which melts at 78–84° C. $[\alpha]_D$=+28° (c=5%, ethanol).

EXAMPLE 6
1,4-Dithia-8-azaspiro[4.5]decane Hydrochloride.

6.1.-8-(Phenylmethyl)-1,4-dithia-8-azaspiro[4.5]-decane.

31.5 g (0.165 mol) of p-toluenesulphonic acid monohydrate and 16.9 g (0.18 mol) of ethanedithiol are added to a solution of 28.35 g (0.150 mol) of 1-benzyl-4-piperidinone in 600 ml of toluene; the mixture is heated under reflux in a Dean-Stark system for 6 h, the solvent is evaporated off, 500 ml of ethyl acetate are added, the solution is washed successively with twice 100 ml of saturated sodium carbonate solution, with water and with brine; it is dried with sodium sulphate and then evaporated to dryness. The residue is purified by chromatography on silica gel with the aid of the 3/97 ethyl acetate/hexane eluent mixture. 17.1 g of 8-(phenylmethyl)-1,4-dithia-8-azaspiro[4.5]decane are obtained in the form of a white solid. Yield 42%. Melting point 51–53° C.

6.2.-1,4-Dithia-8-azaspiro[4.5]decane Hydrochloride.

0.74 ml (0.007 mol) of 1-chloroethyl chloroformate is added to a solution of 1.6 g (0.006 mol) of 8-(phenylmethyl)-1,4-dithia-8-azaspiro-[4.5]decane in 20 ml of dichloroethane; the mixture is heated under reflux for 1.5 h, it is cooled to room temperature, 8 ml of 1 M sodium hydroxide are added, the organic phase is decanted off, the aqueous phase is washed with 25 ml of dichloromethane, the organic phases are dried with sodium sulphate and then evaporated to dryness; the residue is dissolved in 35 ml of methanol and the solution is heated at 60° C. for 40 min; the solvent is evaporated off and the solid obtained is triturated with diisopropyl ether; 0.993 g of 1,4-dithia-8-azaspiro[4.5]decane hydrochloride is thus obtained in the form of a white solid. Yield 78%. Melting point >250° C.

The compounds of the invention are assembled in the following table with their physical characteristics without, however, limiting the scope of the protection. It was possible for them to be prepared according to the processes described.

TABLE
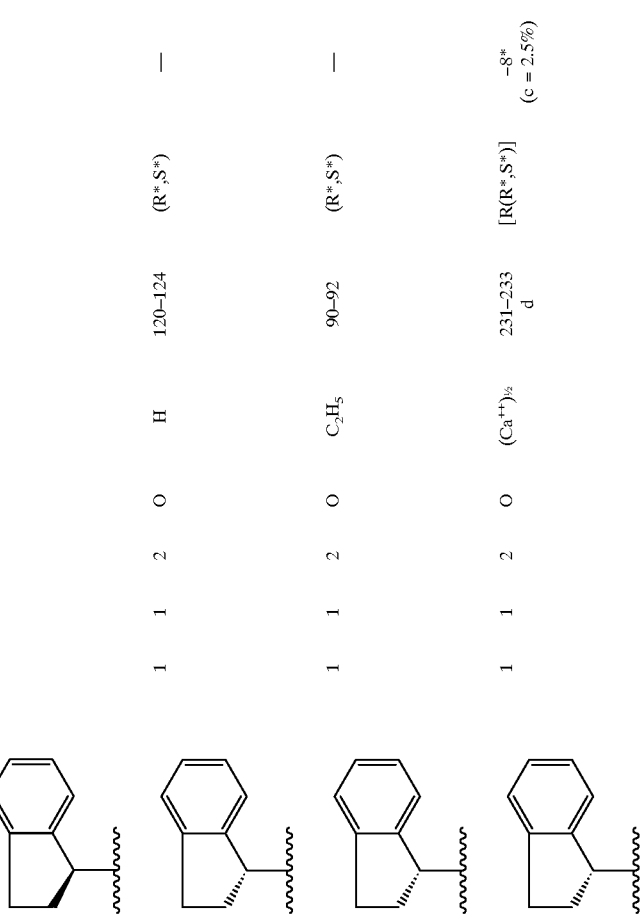
| No. | X | $R_1$ | $R_2$ | $R_3$ | $R_4$ | $R_5$ | $R_6$ | $l$ | $m$ | $n$ | $Y$ | $R_7$ | m.p. (°C.) | Config | $[\alpha]_D°$ c = 5%, Ethanol |
|---|---|---|---|---|---|---|---|---|---|---|---|---|---|---|---|
| 1 | C | $-(CH_2)_4-$ | | H | H | H |  | 1 | 1 | 2 | O | H | 125–129 | (R*,R*) | — |
| 2 | C | $-(CH_2)_4-$ | | H | H | H | | 1 | 1 | 2 | O | H | 120–124 | (R*,S*) | — |
| 3 | C | $-(CH_2)_4-$ | | H | H | H | | 1 | 1 | 2 | O | $C_2H_5$ | 90–92 | (R*,S*) | — |
| 4 | C | $-(CH_2)_4-$ | | H | H | H | | 1 | 1 | 2 | O | $(Ca^{++})_{½}$ | 231–233 d | [R(R*,S*)] | −8* (c = 2.5%) |

TABLE-continued

| No. | X | R₁ | R₂ | R₃ | R₄ | R₅ | R₆ | l | m | n | Y | R₇ | m.p. (°C.) | Config | $[\alpha]_D^\circ$ c = 5%, Ethanol |
|---|---|---|---|---|---|---|---|---|---|---|---|---|---|---|---|
| 5 | C | —(CH₂)₄— | | H | H | H | indanyl | 1 | 1 | 2 | O | H | 137 d | [R(R*,S*)] | −26 |
| 6 | C | —(CH₂)₄— | | H | H | H | indanyl | 1 | 1 | 2 | S | (Ca⁺⁺)½ | 230–232 d | [R(R*,S*)] | — |
| 7 | C | —(CH₂)₄— | | H | H | H | indanyl | 1 | 1 | 2 | O | H | 144–146 d | [S(S*,S*)] | +22 |
| 8 | C | —(CH₂)₄— | | H | H | H | acetyl-indanyl | 1 | 1 | 2 | O | H | 136–142 | [R(R*,S*)] | — |
| 9 | C | —(CH₂)₄— | | H | H | H | (1-hydroxyethyl)-indanyl | 1 | 1 | 2 | O | H | 90 d | [R(R*,S*)] | — |

TABLE-continued
| No. | X | R₁ | R₂ | R₃ | R₄ | R₅ | R₆ | l | m | n | Y | R₇ | m.p. (°C.) | Config | $[\alpha]_D^\circ$ c = 5%, Ethanol |
|---|---|---|---|---|---|---|---|---|---|---|---|---|---|---|---|
| 10 | C | —(CH₂)₄— | | H | H | H | 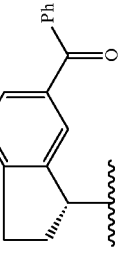 | 1 | 1 | 2 | O | H | 87 d | [R(R*;S*)] | — |
| 11 | C | —(CH₂)₄— | | H | H | H |  | 1 | 1 | 2 | O | H | 116 d | [R(R*;S*)] | — |
| 12 | C | —(CH₂)₄— | | H | H | H | 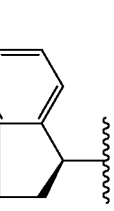 | 1 | 1 | 2 | O | H | 139–141 | [R(R*;R*)] | −19.2 |
| 13 | C | —(CH₂)₄— | | H | H | H | 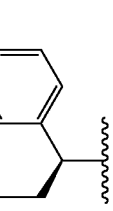 | 1 | 1 | 2 | O | H | 78–84 | [S(S*;R*)] | +28 |

TABLE-continued

| No. | X | R₁ | R₂ | R₃ | R₄ | R₅ | R₆ | l | m | n | Y | R₇ | m.p. (°C.) | Config | $[\alpha]_D°$ c = 5%, Ethanol |
|---|---|---|---|---|---|---|---|---|---|---|---|---|---|---|---|
| 14 | C | CH₃ | CH₃ | H | H | H | indanyl | 1 | 1 | 2 | O | H | 154–160 | (R*,R*) | — |
| 15 | C | CH₃ | CH₃ | H | H | H | indanyl | 1 | 1 | 2 | O | H | 120–125 | (R*,S*) | — |
| 16 | C | CH₃ | CH₃ | H | H | H | indanyl | 1 | 1 | 2 | O | H | 173–175 | [S(S*,S*)] | +17.6 (c = 2.5%) |
| 17 | C | CH₃ | CH₃ | H | H | H | indanyl | 1 | 1 | 2 | O | H | 113–115 | [R(R*,S*)] | — |
| 18 | C | CH₃ | H | H | H | H | indanyl | 1 | 1 | 2 | O | H | 145–148 | (R*,R*) | — |

TABLE-continued

| No. | X | R₁ | R₂ | R₃ | R₄ | R₅ | R₆ | l | m | n | Y | R₇ | m.p. (°C.) | Config | $[\alpha]_D^\circ$ c = 5%, Ethanol |
|---|---|---|---|---|---|---|---|---|---|---|---|---|---|---|---|
| 19 | C | CH₃ | H | H | H | H | indanyl | 1 | 1 | 2 | O | (Ca⁺⁺)½ | 177–191 | (R*,S*) | — |
| 20 | C | CH₃ | H | H | H | H | indanyl | 1 | 1 | 2 | O | H | 194–196 | [S(S*,S*)] | +28* |
| 21 | C | CH₃ | H | H | H | H | indanyl | 1 | 1 | 2 | O | (Ca⁺⁺)½ | 234–238 | [R(R*,S*)] | — |
| 22 | C | Ph—CH₂ | H | H | H | H | indanyl | 1 | 1 | 2 | O | H | 146 | (R*,S*) | — |

TABLE-continued

| No. | X | R₁ | R₂ | R₃ | R₄ | R₅ | R₆ | l | m | n | Y | R₇ | m.p. (°C.) | Config | [α]ᴅ° c = 5%, Ethanol |
|---|---|---|---|---|---|---|---|---|---|---|---|---|---|---|---|
| 23 | C | -CH(CH₃)CH₂CH₂OH | H | H | H | H | indanyl | 1 | 1 | 2 | O | H | 170–200 | (R*,S*) | — |
| 24 | C | -CH(CH₃)CH₂OCH₃ | H | H | H | H | indanyl | 1 | 1 | 2 | O | H | 143–145 | (R*,S*) | — |
| 25 | C | H | H | H | H | H | indanyl | 1 | 1 | 2 | O | Na⁺ | 195–197 | (R*,S*) | — |
| 26 | C | -CO-NH₂ | H | H | H | H | indanyl | 1 | 1 | 2 | O | H | 159–165 | (R*,R*) | — |
| 27 | C | pyrrolyl | H | H | H | H | indanyl | 1 | 1 | 2 | O | H | 133–137 | (R*,R*) | — |

TABLE-continued

| No. | X | R₁ | R₂ | R₃ | R₄ | R₅ | R₆ | l | m | n | Y | R₇ | m.p. (°C.) | Config | $[\alpha]_D^\circ$ c = 5%, Ethanol |
|---|---|---|---|---|---|---|---|---|---|---|---|---|---|---|---|
| 28 | C | pyrrole | H | H | H | H | indanyl | 1 | 1 | 2 | O | (Ca⁺⁺)½ | 208 | (R*,S*) | — |
| 29 | C | tetrahydrofuranyl | H | H | H | H | indanyl | 1 | 1 | 2 | O | H | 121–122 | [R(R*,S*)] | — |
| 30 | C | tetrahydrofuranyl | H | H | H | H | indanyl | 1 | 1 | 2 | O | H | 139–144 | [S(S*,S*)] | — |
| 31 | O | — | — | H | H | H | indanyl | 0 | 0 | 2 | O | Na⁺ | 205–210 | (R*,S*) | — |

TABLE-continued

| No. | X | R₁ | R₂ | R₃ | R₄ | R₅ | R₆ | l | m | n | Y | R₇ | m.p. (°C.) | Config | $[\alpha]_D°$ c = 5%, Ethanol |
|---|---|---|---|---|---|---|---|---|---|---|---|---|---|---|---|
| 32 | S | — | — | H | H | H | indanyl | 0 | 0 | 2 | O | H | 148 | (R*,S*) | — |
| 33 | SO₂ | — | — | H | H | H | indanyl | 0 | 0 | 2 | O | Na⁺ | >250 | (R*,S*) | — |
| 34 | N | CH₃ | — | H | H | H | indanyl | 1 | 0 | 2 | O | H | 100–120 | (R*,S*) | — |
| 35 | C | H | cyclohexyl | H | H | H | indanyl | 1 | 1 | 1 | O | H | 158–160 | (R*,R*) | — |
| 36 | C | H | cyclohexyl | H | H | H | indanyl | 1 | 1 | 1 | O | (Ca⁺⁺)½ | >250 | (R*,S*) | — |

TABLE-continued

| No. | X | R₁ | R₂ | R₃ | R₄ | R₅ | R₆ | l | m | n | Y | R₇ | m.p. (°C.) | Config | [α]_D° c = 5%, Ethanol |
|---|---|---|---|---|---|---|---|---|---|---|---|---|---|---|---|
| 37 | C | H | (cyclohexene) | | H | H | (indanyl) | 1 | 1 | 1 | O | H | 184–186 | (R*,R*) | — |
| 38 | C | H | (cyclohexene) | | H | H | (indanyl) | 1 | 1 | 1 | O | H | 102–108 | (R*,S*) | — |
| 39 | C | H | — | H | H | H | (indanyl) | 1 | 1 | 1 | O | Na⁺ | 232–236 | (R*,S*) | — |
| 40 | C | H | — | — | H | H | (indanyl) | 1 | 1 | 1 | O | H | 135–138 | (R*,S*) | — |

TABLE-continued

| No. | X | R$_1$ | R$_2$ | R$_3$ | R$_4$ | R$_5$ | R$_6$ | l | m | n | Y | R$_7$ | m.p. (°C.) | Config | $[\alpha]_D^\circ$ c = 5%, Ethanol |
|---|---|---|---|---|---|---|---|---|---|---|---|---|---|---|---|
| 41 | C | H | OH | OH | H | H | indanyl | 1 | 1 | 1 | O | Na$^+$ | >250 | (R*,S*) | — |
| 42 | C | —(CH$_2$)$_5$— | | OH | H | H | indanyl | 1 | 1 | 2 | O | H | 132–134 | (R*,S*) | — |
| 43 | C | —(CH$_2$)$_5$— | | H | H | H | indanyl | 1 | 1 | 1 | O | H | 110–113 | (R*,S*) | — |
| 44 | C | —(CH$_2$)$_4$— | | H | H | H | indanyl | 1 | 1 | 1 | O | H | 142–144 | (R*,R*) | — |
| 45 | C | —O(CH$_2$)$_2$O— | | H | H | H | indanyl | 1 | 1 | 2 | O | H | 156–158 | (R*,R*) | — |

TABLE-continued

| No. | X | R₁ | R₂ | R₃ | R₄ | R₅ | R₆ | l | m | n | Y | R₇ | m.p. (°C.) | Config | $[\alpha]_D^\circ$ c = 5%, Ethanol |
|---|---|---|---|---|---|---|---|---|---|---|---|---|---|---|---|
| 46 | C | —O(CH₂)₂O— | | H | H | H | indanyl | 1 | 1 | 2 | O | Na⁺ | >250 | (R*,S*) | — |
| 47 | C | —O(CH₂)₂O— | | H | H | H | indanyl | 1 | 1 | 2 | O | H | 200–206 | [S(S*,S*)] | +26.4* |
| 48 | C | —O(CH₂)₂O— | | H | H | H | indanyl | 1 | 1 | 2 | O | Na⁺ | >250 | [R(R*,S*)] | — |
| 49 | C | —S(CH₂)₂S— | | H | H | H | indanyl | 1 | 1 | 2 | O | H | 121 | (R*,S*) | — |

TABLE-continued

| No. | X | $R_1$ | $R_2$ | $R_3$ | $R_4$ | $R_5$ | $R_6$ | $l$ | $m$ | $n$ | $Y$ | $R_7$ | m.p. (°C.) | Config | $[\alpha]_D^\circ$ c = 5%, Ethanol |
|---|---|---|---|---|---|---|---|---|---|---|---|---|---|---|---|
| 50 | C | —S(CH$_2$)$_2$S— | | H | H | H | indanyl | 1 | 1 | 2 | O | H | 200–202 | [S(S*,S*)] | — |
| 51 | C | —S(CH$_2$)$_2$S— | | H | H | H | indanyl | 1 | 1 | 2 | O | H | 120–123 | [R(R*,S*)] | −41.6* |
| 52 | C | —SO$_2$(CH$_2$)$_2$SO$_2$— | | H | H | H | indanyl | 1 | 1 | 2 | O | H | 215–220 | [R(R*,S*)] | — |
| 53 | C | —C(=O)NH—CH$_2$— | | H | H | H | indanyl | 1 | 1 | 2 | O | H | 102 d | [R(R*,S*)] | — |
| 54 | C | —(CH$_2$)$_4$— | | H | H | OH | indanyl | 1 | 1 | 2 | O | H | 90 | | −14.4 (c = 2.5%) |

TABLE-continued

| No. | X | $R_1$ | $R_2$ | $R_3$ | $R_4$ | $R_5$ | $R_6$ | l | m | n | Y | $R_7$ | m.p. (°C.) | Config | $[\alpha]_D^\circ$ c = 5%, Ethanol |
|---|---|---|---|---|---|---|---|---|---|---|---|---|---|---|---|
| 55 | C | H | | norbornene | H | H | indanyl | 1 | 1 | 1 | O | $Na^+$ | 211 d | (R*,S*) | — |
| 56 | C | H | | norbornane | H | H | indanyl | 1 | 1 | 1 | O | H | 171–174 d | (R*,S*) | — |
| 57 | C | —(CH$_2$)$_4$— | | H | H | indanyl | H | 1 | 1 | 2 | O | H | 124 d | [R(R*,S*)] | −74.4 |
| 58 | C | H | | dioxolane | H | H | benzyl | 1 | 1 | 1 | O | $Na^+$ | 193–198 | (S) | +1.6 (c = 2.5%) |

TABLE-continued

| No. | X | $R_1$ | $R_2$ | $R_3$ | $R_4$ | $R_5$ | $R_6$ | l | m | n | Y | $R_7$ | m.p. (°C.) | Config | $[\alpha]_D°$ c = 5%, Ethanol |
|---|---|---|---|---|---|---|---|---|---|---|---|---|---|---|---|
| 59 | C | H | \multicolumn{2}{c}{–O–C(=O)–O–} | | H | H | benzyl | 1 | 1 | 1 | O | H | 142–145 | (S) | −18* |
| 60 | C | H | \multicolumn{2}{c}{–O–CH$_2$–O–} | | H | H | benzyl | 1 | 1 | 1 | O | H | 107 | (R,S) | — |
| 61 | C | H | \multicolumn{2}{c}{–O–CH$_2$–O–} | | H | H | indanyl | 1 | 1 | 1 | O | H | 150 d | (R*,S*) | — |
| 62 | C | —(CH$_2$)$_4$— | | | H | H | pyrrolizinyl | 1 | 1 | 2 | O | H | 139–142 | (R*,R*) | — |

TABLE-continued

| No. | X | R₁ | R₂ | R₃ | R₄ | R₅ | R₆ | l | m | n | Y | R₇ | m.p. (°C.) | Config | [α]ᴅ° c = 5%, Ethanol |
|---|---|---|---|---|---|---|---|---|---|---|---|---|---|---|---|
| 63 | C | —(CH₂)₄— | | H | H | H | pyrrolizidine | 1 | 1 | 2 | O | H | 139–142 | (R*,S*) | — |
| 64 | C | H | cyclohexyl | | H | H | pyrrolizidine | 1 | 1 | 1 | O | H | 56–58 | (R*,S*) | — |
| 65 | C | H | cyclohexenyl | | H | H | pyrrolizidine | 1 | 1 | 1 | O | H | 155–157 | (R*,S*) | — |
| 66 | C | —(CH₂)₄— | | H | H | H | benzisoxazoline | 1 | 1 | 2 | O | H | 144–146 | (R*,S*) | — |

TABLE-continued
| No. | X | $R_1$ | $R_2$ | $R_3$ | $R_4$ | $R_5$ | $R_6$ | $l$ | $m$ | $n$ | $Y$ | $R_7$ | m.p. (°C.) | Config | $[\alpha]_D°$ c = 5%, Ethanol |
|---|---|---|---|---|---|---|---|---|---|---|---|---|---|---|---|
| 67 | C | —(CH$_2$)$_4$— | | H | H | H | 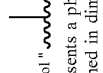 | 1 | 1 | 2 | O | H | 171–173 | (R*,S*) | — |
In this table:
d = decomposition
the symbol " ⁓⁓⁓ " represents the position of a carbon-carbon bond
Ph represents a phenyl
*performed in dimethyl sulphoxide The compounds of the invention were tested in various biological trials.

They were in particular subjected to a test for hypoglycaemic activity in rats. This trial was carried out on rats that had been kept fasting for 20 h. The test products are administered by the oral route; blood samples are collected from the tail 0.5, 1, 2, 3, 5 and 7 h after administration of the product, according to the method described by H. Ohnota in The Journal of Pharmacology and Experimental Therapeutics, 269, No. 2, 489–495 (1994).

The compounds of the invention reduce by 30 to 40% the basal glycaemia at doses of between 0.1 and 10 mg/kg.

They were also subjected to a test for antihyperglycaemic activity in rats according to the method described by R. S. Ho et al., in Arch. Int. Pharmacodyn. 237, 98 (1979).

This trial is carried out on mice that had been kept fasting for 20 h. The test products are administered by the oral route 30 min before the administration of a glucose overload (1.5 g/kg). The animals are sacrificed by decapitation 30 min after the glucose overload and their glycaemia is determined as above.

The median effective doses ($ED_{50}$) of the compounds of the invention are between 0.1 and 10 mg/kg. In this trial, the reference compound KAD1229 has a median effective dose of 1.5 mg/kg.

The in vivo activity of the compounds of the present invention was studied in an experimental model of plantar inflammation in rats.

Inflammatory oedema of the paw of rats induced by the intradermal injection of carrageenan (CAR) (1k, v/v) is obtained and evaluated according to the method of Winter C. A., and Risley E. A. (Carrageenan-induced edema in the hindpaw of rats as an assay for anti-inflammatory drugs. Proc. Soc. Axp. Biol. Med, 19632, 11, 544–547).

The compounds of the invention are given orally 1 hour before the injection of CAR. A 1% solution of CAR in a saline solution is injected by the s.c. route into the subplantar part of the right hindpaw of rats.

The volume resulting from the inflammatory reaction is measured by plethysmography after 1.5, 3 and 4.5 hours from the injection of CAR.

The compounds of the invention at doses of is between 0.5 and 10 mg/kg by the oral route confer lasting inhibition of the inflammation induced (between 1.5, 3 and 4.5 hours after the injection of CAR) of between 20 and 90% relative to the control.

The results show that the compounds of the invention exhibit "in vivo" hypo- and antihyperglycaemic, and anti-inflammatory properties. They can therefore be used in the treatment of hyperglycaemia, diabetes, obesity and inflammation. In the case of inflammation, they can be used more particularly in neuropathies in diabetics, polyarthritis, osteoarthritis, lumbago, traumatological pain, inflammation in the ENT domain.

The compounds of the invention may be provided, in combination with any appropriate excipient, in any form suitable for administration by the oral or parenteral route, for example in the form of tablets, gelatin capsules, sugar-coated tablets or oral or injectable solutions.

The compounds of the invention may be administered in daily doses of between about 1 and 100 mg in adults by the oral route, or between about 0.1 and 100 mg by the parenteral route.

What is claimed is:

1. A compound of general formula (I)

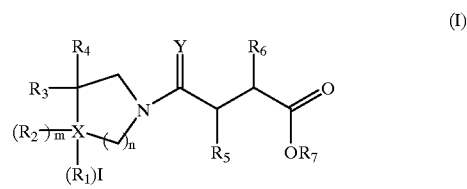

in which:

$R_1$ represents a hydrogen atom, hydroxyl, a $C_{1-4}$ alkyl $C_{1-4}$ hydroxyalkyl, $C_{4-7}$ cycloalkyl or $C_{1-4}$ alkyloxy ($C_{1-4}$ alkyl) group, an aminocarbonyl group, a benzyl, a heterocycloalkyl or heteroaryl group comprising from 4 to 5 carbon atoms and a heteroatom selected from the group consisting of nitrogen, sulphur and oxygen, the heterocycloalkyl or heteroaryl group being optionally substituted with one or two substituents selected from the group consisting of a hydroxyl, a $C_{1-4}$ alkyl group and a halogen;

$R_2$, $R_3$ and $R_4$, which may be identical or different, represent independently of each other a hydrogen atom, a $C_{1-4}$ alkyl group, a $C_{4-7}$ cycloalkyl group, a hydroxyl group, an aminocarbonyl group or a heteroaryl group comprising from 4 to 5 carbon atoms and a heteroatom selected from the group consisting of nitrogen, sulphur and oxygen, the heteroaryl group being optionally substituted with one or two substituents selected from the group consisting of a hydroxyl group, a $C_{1-4}$ alkyl group and a halogen;

or $R_1$ and $R_2$ together form a $C_{3-6}$ alkylene group, a $C_{2-3}$ alkylenedioxy group, a $C_{2-3}$ alkylenedithio group, —($O_2$)S—$C_{2-3}$ alkylene-S($O_2$)— or a group —$CH_2NHC(O)CH_2$—;

or $R_2$ and $R_3$ together form a propylene or butylene group, a $C_{1-3}$ alkylenedioxy group, a carbonyldioxy group or a 2-butenylene;

or $R_2$ and $R_3$ together form with the atoms carrying them a norbornane or a 5-norbornene or a bond in order to give a double bond between the atoms carrying them, X being a carbon atom;

$R_5$ represents a hydrogen atom, a hydroxyl group or, when $R_6$ represents a hydrogen, a 1-indanyl group;

$R_6$ represents an aromatic group chosen from the following groups:

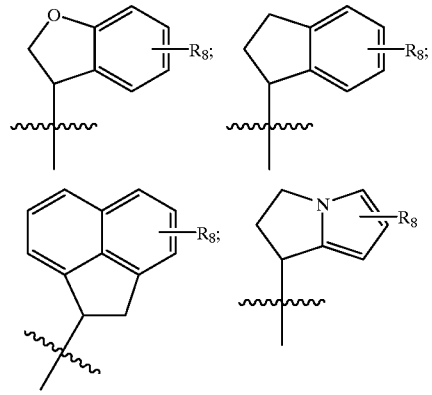

or, when $R_2$ and $R_3$ together form a $C_{1-3}$ alkylenedioxy or carbonyldioxy group, a benzyl optionally substituted with one or two substituents selected from the group consisting of a halogen and a $C_{1-4}$ alkyl group, or $R_6$ represents a hydrogen, when $R_5$ represents a 1-indanyl group;

$R_7$ represents a hydrogen atom or a $C_{1-4}$ alkyl group;

$R_8$ represents a hydrogen, an acetyl, a benzoyl, a $C_{1-4}$ alkyl group, optionally substituted with a hydroxyl; or a $C_{1-2}$ alkylphenyl group, optionally substituted on the alkyl group with a hydroxyl, X represents a carbon, nitrogen, oxygen or sulphur atom or a sulphonyl group, Y represents an oxygen or sulphur atom, n is equal to 1 or 2; l is equal to 1 and m is equal to 0 when X represents a nitrogen atom; l and m are equal to 0 when X represents a sulphur or oxygen atom or a sulphonyl; they are equal to 1 when X represents a carbon atom, and optionally in the form of an enanitiomer, a diastereoisomer or a mixture of these various forms, or the addition salts with pharmaceutically acceptable bases or acids of one of these forms.

2. A compound according to claim 1 wherein n is equal to 2 and $R_7$ is a hydrogen atom.

3. A compound according to claim 1 wherein it is in the form of a sodium or calcium salt, such that $R_7$ represents a sodium or calcium atom.

4. [R-(R*,S*)]-α-(2,3-Dihydro-1H-inden-1-yl)-γ-oxo-8-azaspiro[4.5]decane-8-butanoic acid according to claim 1.

5. [S-(S*,R*)]-α-(2,3-Dihydro-1H-inden-1-yl)-γ-oxo-8-azaspiro[4.5]decane-8-butanoic acid according to claim 1.

6. [R-(R*,R*)]-α-(2,3-Dihydro-1H-inden-1-yl)-γ-oxo-8-azaspiro[4.5]decane-8-butanoic according to claim 1.

7. [S-(S*,S*)]-α-(2,3-Dihydro-1H-inden-1-yl)-γ-oxo-8-azaspiro[4.5]decane-8-butanoic acid according to claim 1.

8. A process for the preparation of a compound of formula (I), according to claim 1 wherein a compound of formula (II)

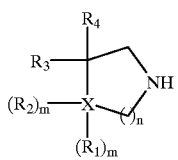

(II)

in which $R_1$, $R_2$, $R_3$, $R_4$, X, l, m and n are defined as in formula (I), is reacted with a compound of general formula (III)

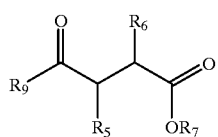

(III)

in which $R_7$ represents a $C_{1-4}$ alkyl group, $R_5$ and $R_6$ are defined as in formula (I) and $R_9$ represents a halogen atom or a hydroxyl group, optionally in the presence of an activating agent, to give the compounds of formula (I) in which $R_1$, $R_2$, $R_3$, $R_4$, $R_5$, $R_6$, $R_7$, X, l, m and n are as defined above, optionally followed by a thiation reaction to give the compounds of formula (I) in which Y is a sulphur atom, and by hydrolysis to give the compounds of formula (I), in which $R_7$ is a hydrogen atom.

9. A method for the treatment of hyperglycaemia, diabetes, obesity or inflammation which comprises administering to a patient in need of such treatment an effective amount of a compound according to claim 1.

10. A pharmaceutical composition which comprises at least one compound according to claim 1 together with one or more appropriate excipients.

11. A compound according to claim 1 wherein $R_2$, $R_3$ and $R_4$ represent, independently of each other, a hydrogen atom, a $C_{1-4}$ alkyl group or a hydroxyl group.

12. A compound according to claim 11 wherein $R_4$ represents a hydrogen and $R_5$ represents a hydrogen.

13. A compound according to one of claim 1 wherein $R_6$ represents an aromatic group other than a benzyl.

14. A compound according to claim 13 wherein $R_6$ represents an indanyl.

15. A compound according to claim 14 wherein $R_1$ and $R_2$ together form a $C_{3-6}$ alkylene group.

16. A method for the treatment of hyperglycaemia, diabetes, obesity or inflammation which comprises administering to a patient in need of such treatment an effective amount of a compound according to claim 2.

17. A method for the treatment of hyperglycaemia, diabetes, obesity or inflammation which comprises administering to a patient in need of such treatment an effective amount of a compound according to claim 3.

18. A method for the treatment of hyperglycaemia, diabetes, obesity or inflammation which comprises administering to a patient in need of such treatment an effective amount of a compound according to claim 4.

19. A method for the treatment of hyperglycaemia, diabetes, obesity or inflammation which comprises administering to a patient in need of such treatment an effective amount of a compound according to claim 5.

20. A method for the treatment of hyperglycaemia, diabetes, obesity or inflammation which comprises administering to a patient in need of such treatment an effective amount of a compound according to claim 6.

21. A method for the treatment of hyperglycaemia, diabetes, obesity or inflammation which comprises administering to a patient in need of such treatment an effective amount of a compound according to claim 7.

22. A method for the treatment of hyperglycaemia, diabetes, obesity or inflammation which comprises administering to a patient in need of such treatment an effective amount of a compound according to claim 11.

23. A method for the treatment of hyperglycaemia, diabetes, obesity or inflammation which comprises administering to a patient in need of such treatment an effective amount of a compound according to claim 12.

24. A method for the treatment of hyperglycaemia, diabetes, obesity or inflammation which comprises administering to a patient in need of such treatment an effective amount of a compound according to claim 13.

25. A method for the treatment of hyperglycaemia, diabetes, obesity or inflammation which comprises administering to a patient in need of such treatment an effective amount of a compound according to claim 14.

26. A method for the treatment of hyperglycaemia, diabetes, obesity or inflammation which comprises administering to a patient in need of such treatment an effective amount of a compound according to claim 15.

27. A pharmaceutical composition which comprises at least one compound according to claim 2 together with one or more appropriate excipients.

28. A pharmaceutical composition which comprises at least one compound according to claim 3 together with one or more appropriate excipients.

29. A pharmaceutical composition which comprises at least one compound according to claim 4 together with one or more appropriate excipients.

30. A pharmaceutical composition which comprises at least one compound according to claim 5 together with one or more appropriate excipients.

31. A pharmaceutical composition which comprises at least one compound according to claim 6 together with one or more appropriate excipients.

32. A pharmaceutical composition which comprises at least one compound according to claim 7 together with one or more appropriate excipients.

33. A pharmaceutical composition which comprises at least one compound according to claim 11 together with one or more appropriate excipients.

34. A pharmaceutical composition which comprises at least one compound according to claim 12 together with one or more appropriate excipients.

35. A pharmaceutical composition which comprises at least one compound according to claim 13 together with one or more appropriate excipients.

36. A pharmaceutical composition which comprises at least one compound according to claim 14 together with one or more appropriate excipients.

37. A pharmaceutical composition which comprises at least one compound according to claim 15 together with one or more appropriate excipients.

* * * * *